(12) United States Patent
Palmer et al.

(10) Patent No.: US 8,137,377 B2
(45) Date of Patent: *Mar. 20, 2012

(54) EMBOLIC BASKET

(75) Inventors: Olin Palmer, Mountain View, CA (US); Christopher T. Shen, Stanford, CA (US)

(73) Assignee: Abbott Laboratories, Abbott Park, IL (US)

( * ) Notice: Subject to any disclaimer, the term of this patent is extended or adjusted under 35 U.S.C. 154(b) by 995 days.

This patent is subject to a terminal disclaimer.

(21) Appl. No.: 12/111,911

(22) Filed: Apr. 29, 2008

(65) Prior Publication Data
US 2008/0275498 A1 Nov. 6, 2008

Related U.S. Application Data

(60) Continuation of application No. 11/317,930, filed on Dec. 22, 2005, now abandoned, which is a continuation of application No. 10/423,300, filed on Apr. 25, 2003, now Pat. No. 7,004,956, which is a division of application No. 09/939,205, filed on Aug. 24, 2001, now Pat. No. 6,575,997, which is a continuation-in-part of application No. 09/469,431, filed on Dec. 23, 1999, now Pat. No. 6,402,771.

(51) Int. Cl.
*A61M 29/00* (2006.01)
(52) U.S. Cl. ........................................ 606/200
(58) Field of Classification Search ............... 606/1, 113, 606/114, 127, 159, 200; 600/434, 585
See application file for complete search history.

(56) References Cited

U.S. PATENT DOCUMENTS

| | | | |
|---|---|---|---|
| 2,943,626 | A | 7/1960 | Dormia |
| 3,952,747 | A | 4/1976 | Kimmell, Jr. |
| 4,347,846 | A | 9/1982 | Dormia |
| 4,452,908 | A | 6/1984 | Ball et al. |
| 4,494,531 | A | 1/1985 | Gianturco |
| 4,611,594 | A | 9/1986 | Grayhack et al. |
| 4,612,931 | A | 9/1986 | Dormia |
| 4,619,246 | A | 10/1986 | Molgaard-Nielsen et al. |
| 4,643,184 | A | 2/1987 | Mobin-Uddin |
| 4,650,466 | A | 3/1987 | Luther |

(Continued)

FOREIGN PATENT DOCUMENTS
EP 0427429 A3 9/1991
(Continued)

OTHER PUBLICATIONS

Dilitation of the Carotid Artery by A Temporary Carotid Filter by A. Beck, St. Milic, A.M. Spagnoli, Nov.-Dec. Issue of OPLITAI, An International Journal on Military Medicine and Health Emergencies, pp. 67-74.

(Continued)

*Primary Examiner* — Kevin T Truong
(74) *Attorney, Agent, or Firm* — Fulwider Patton LLP; Jonathan Feuchtwang

(57) ABSTRACT

An intravascular basket device for use in capturing either naturally occurring or foreign debris found in blood vessels or other regions of the body. The basket device is fabricated from a tube and includes a mid-section having at least one ring configured in an alternating V-pattern. The basket device specifically embodies structure that provides enhanced radial opening and angular resistance to collapse.

12 Claims, 7 Drawing Sheets

U.S. PATENT DOCUMENTS

| | | |
|---|---|---|
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,865,017 A | 9/1989 | Shinozuka |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,154,705 A * | 10/1992 | Fleischhacker et al. ...... 600/585 |
| 5,158,548 A | 10/1992 | Lau |
| 5,160,342 A | 11/1992 | Reger et al. |
| 5,171,233 A | 12/1992 | Amplatz et al. |
| 5,192,286 A | 3/1993 | Phan et al. |
| 5,234,458 A | 8/1993 | Metais |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,486,183 A | 1/1996 | Middleman et al. |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,509,923 A | 4/1996 | Middleman et al. |
| 5,549,626 A | 8/1996 | Miller et al. |
| 5,601,572 A | 2/1997 | Middleman et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,706,826 A * | 1/1998 | Schwager ...................... 600/585 |
| 5,709,704 A | 1/1998 | Nott et al. |
| 5,720,754 A | 2/1998 | Middleman et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,820,628 A | 10/1998 | Middleman et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,895,398 A | 4/1999 | Wensel et al. |
| 5,897,567 A | 4/1999 | Ressemann et al. |
| 5,902,263 A | 5/1999 | Patterson et al. |
| 5,904,690 A | 5/1999 | Middleman et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita |
| 6,168,603 B1 | 1/2001 | Leslie et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |

| Patent No. | Date | Inventor |
|---|---|---|
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,205 B1 * | 5/2002 | Samson et al. ............... 606/200 |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Denison et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Evans et al. |
| 6,638,293 B1 | 10/2003 | Makower et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |

| Patent | Date | Inventor |
|---|---|---|
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Weber et al. |
| 6,699,260 B2 | 3/2004 | Dubrul et al. |
| 6,702,834 B1 | 3/2004 | Boylen et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi et al. |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |

| | | |
|---|---|---|
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Esksuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082697 A1 | 4/2004 | Broome et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |

| | | |
|---|---|---|
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| FR | 2768326 | 3/1999 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/72205 | 10/2001 |
| WO | WO01/87183 | 11/2001 |

OTHER PUBLICATIONS

Minibasket for Percutaneous Embolectomy and Filter ProtectionAgainst Distal Embolization: Technical Note.

* cited by examiner

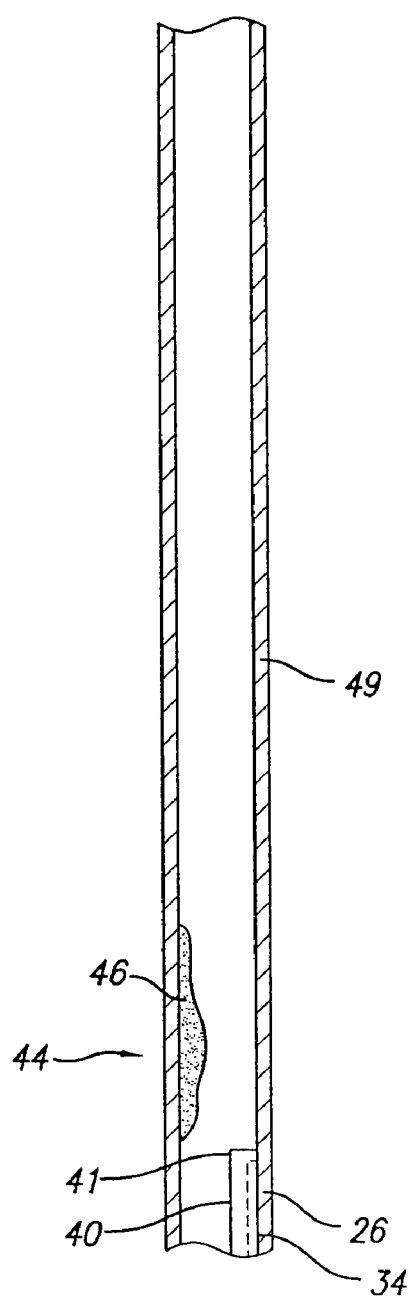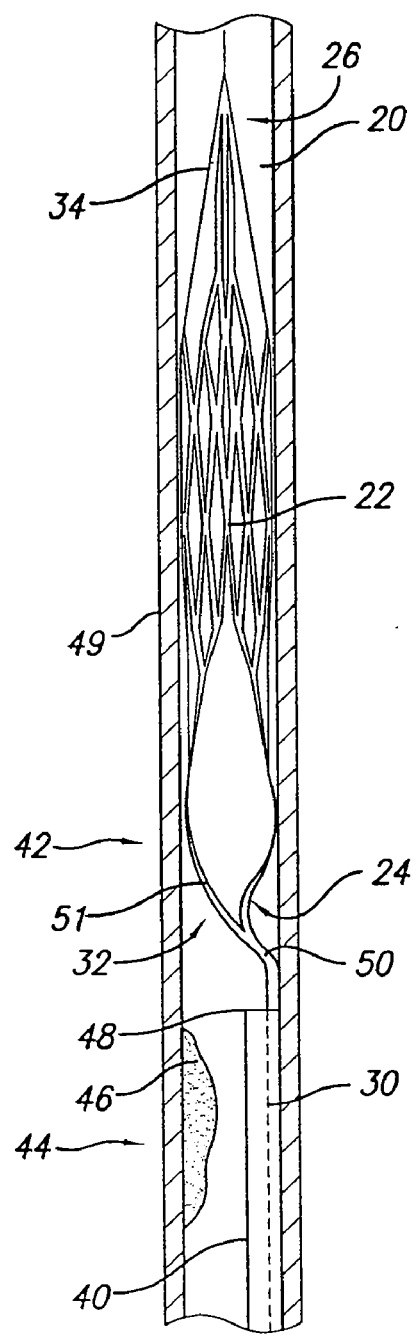

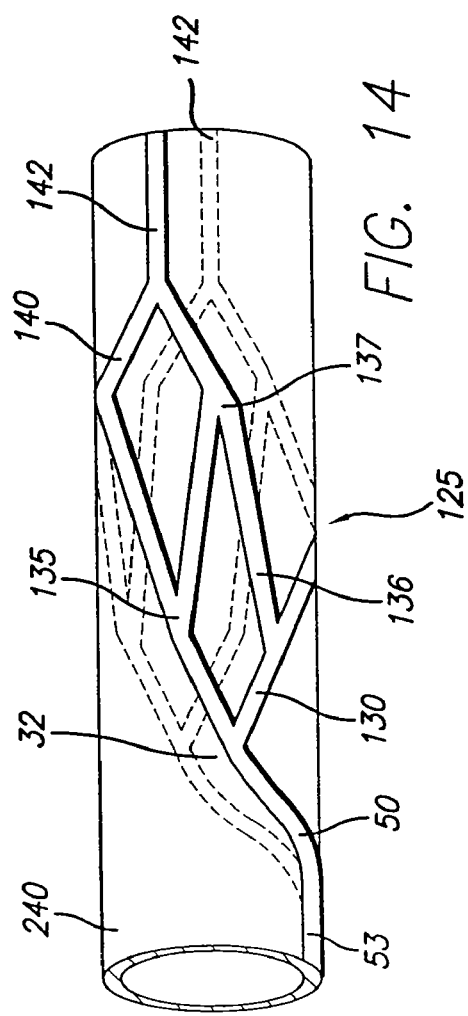
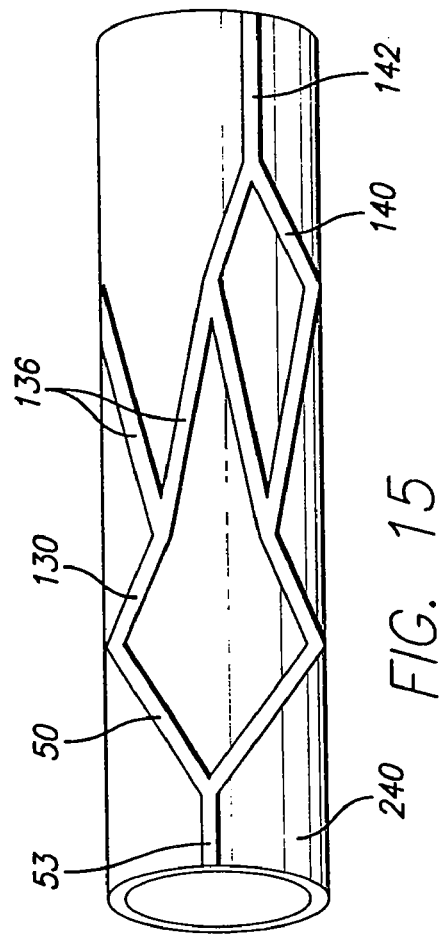

EMBOLIC BASKET

CROSS-REFERENCES TO RELATED APPLICATIONS

This is a continuation of U.S. Ser. No. 11/317,930, filed on Dec. 22, 2005 now abandoned; which is a continuation of U.S. Ser. No. 10/423,300, filed on Apr. 25, 2003, U.S. Pat. No. 7,004,956, issued on Feb. 28, 2006; which is a divisional of U.S. Ser. No. 09/939,205, filed on Aug. 24, 2001, U.S. Pat. No. 6,575,997, issued on Jun. 10, 2003; which is a continuation-in-part of U.S. Ser. No. 09/469,431, filed on Dec. 23, 1999, U.S. Pat. No. 6,402,771, which issued on Jun. 11, 2002, the contents of which are hereby incorporated by reference.

BACKGROUND OF THE INVENTION

The present invention relates generally to intravascular devices and systems and more particularly, basket devices which can be used to capture embolic material or thrombi found in blood vessels.

The intravascular basket device and system of the present invention is particularly useful when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. The basket device is also suited for the removal of clots adhering to vessel walls. The device is also suitable for removal of misplaced coils or other foreign material. While the basket device and system of the present invention is particularly useful in the cerebral vasculature and neurovasculature, the invention can be used in conjunction with any vascular interventional procedure in which there is an embolic risk. Additionally, it can be used in any region of the body where removal of debris or foreign material is indicated. Having a patterned body cut from a single tube element, the basket device allows for an enhanced radial opening into the basket body that provides for greater ease of embolic capture. Additionally the patterned body embodies greater stability during use by resisting the natural tendency to collapse as seen in most prior art snares during a typical operation.

A variety of non-surgical interventional procedures have been developed over the years for opening stenosed or occluded blood vessels in a patient caused by the build-up of plaque or other substances on the wall of the blood vessel. Such procedures usually involve the remote introduction of the interventional device into the lumen of the artery, usually through a catheter. In typical carotid PTA procedures, a guiding catheter or sheath is percutaneously introduced into the cardiovascular system of a patient through the femoral artery and advanced, for example, through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. A first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, cerebral vasculature, or neurovasculature, the release of emboli into the circulatory system can be extremely dangerous and sometimes fatal to the patient. Naturally occurring debris can also be highly dangerous to a patient. That is, debris which travels through the blood vessel as a natural result of bodily functions and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

In addition, the retrieval of fragmented clot may be incomplete, also resulting in emboli and distal occlusions, and further, access through tortuous lumens may prove difficult. Laser-based disruption devices employ the photo-acoustic effect to fragment clot. Local disruption may open up a proximal occlusion but also may cause significant distal emboli.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could otherwise cause problems to the patient's vasculature. Other techniques which have had some limited success include the placement of a filter or trap downstream from the treatment site to capture embolic debris before it reaches the smaller blood vessels downstream. However, there have been problems associated with conventional filtering systems as well. In particular, certain previously developed filtering devices do not optimize the area for embolic collection. That is, conventional filtering devices may not present a collection device that spans the entirety of the vessel or it may include supporting structure that itself impedes emboli collection. Certain other devices do not embody sufficient angular resistance to collapse.

Moreover, thrombectomy and foreign matter removal devices have been disclosed in the art. However, in addition to suffering from the same disadvantages as certain conventional filter devices, such devices have been found to have structures which are either highly complex such as with multiple components or highly convoluted geometry or lacking in sufficient or effective expansion and retraction capabilities. Disadvantages associated with the devices having highly complex structure such as with multiple components or highly convoluted geometry include difficulty in manufacturability as well as use in conjunction with microcatheters. Other devices with less coverage can pull through clots due in part to the lack of experience in using the same or otherwise lack an expanded profile that is adequate to capture clots or foreign bodies.

Furthermore, in current interventional radiology practice, the need arises to remove a variety of objects from intraluminal spaces. Among these are embolic coils, guidewire tips, distal catheter segments, thrombus and other vascular emboli, few of which can be readily removed with current devices.

Thrombo-embolic materials can be friable, amorphous, and/or lubricious in nature contributing to this difficulty. Most current therapies rely on grasping, fragmenting, or dissolving the blood-based obstructions. Among the grasping devices are the loop snares and the wire basket snares. These devices may have limited effectiveness, due in part to the lack of encapsulation. Objects are difficult to grasp within these devices, and friable objects, e.g. blood-based blockages, tend to fragment when grasped or pulled, introducing multiple emboli.

Lytic drugs are also used to dissolve blood-based obstructions. These typically have the disadvantages of lengthy treatment/infusion times to remove the obstruction (>3 hrs.), production of emboli, and the potential for systemic iatrogenic bleeding as a side effect of the drug usage. Also, these drugs are not typically effective in removing obstructions that are not blood-based.

What has been needed is a reliable intravascular basket device and system for use when treating blood vessels. The basket devices should be capable of capturing any naturally occurring embolic debris or that which may be released into the bloodstream during an interventional treatment, while minimizing profile during delivery and maximizing coverage when deployed to safely contain the debris until the basket device is removed from the patient's vasculature. The devices should embody an expanded profile that presents a consistent radial opening that completely occupies the vessel at the repair site as well as structure for effectively resisting collapse. Moreover, such devices should be relatively easy to deploy and remove from the patient's vasculature and also should be capable of being used in narrow and very distal vasculature such as the cerebral vasculature. The following invention addresses these needs.

SUMMARY OF THE INVENTION

Briefly and in general terms, the present invention is directed towards a basket for removing undesired material or objects and restoring patency of blood vessels. The basket is a linked or monolithic framework of thin struts that is radially expansible. The basket of the present invention embodies a structure that provides a consistent radial opening as well as improved radial and angular resistance to collapse. That is, as the device is pulled such as through a vessel, the entrance thereto will not fall back or tip over. Moreover, the basket device maintains clearance in its interior space along its length allowing the material or objects to enter and be captured.

In one aspect of the invention, the basket includes struts with very small widths and thicknesses and rings with very small widths and thicknesses but large expansion ratios. It is particularly beneficial to manufacture the basket from a piece of tube stock, as opposed to prior art wire baskets, because the resulting basket is more ordered upon compression, returns to its expanded state more reliably and is quicker to manufacture. The body of the basket device is defined by a plurality of openings bounded by generally longitudinally and generally circumferentially extending members. A proximally extending member is attached to an elongate wire and the assembly is contemplated to be used in conjunction with a generally tubular delivery catheter. In this aspect the body provides enhanced stability at the proximal transition between the wire and the proximally extending members because the design may allow for varying lengths and widths of the proximally extending members. The basket may be manufactured from a single tubular element or from a sheet to form a desired configuration.

Overall, the intent of the invention is to provide a structure that has the capacity to engage, encompass and retain naturally occurring or foreign bodies while having a minimal profile that can traverse easily and repeatedly through a standard microcatheter across tortuous anatomy. The device embodies superior flexibility to be deployed and retrieved consistently across difficult anatomy while being able to retain captured material. The inner diameter of the device is heat-set to a pre-determined size. It is envisioned that there be a family of devices that have varying strut lengths, thicknesses, flexibility, and diameters as deemed appropriate for the specific type of vascular or non-vascular setting for which the device is to be used.

In a presently preferred embodiment, the basket device is self-expanding and includes a mid-section that forms a generally tubular profile. The proximally extending member projects as an axial extension of a line at the surface of the cylinder generally defining the substantially tubular portion to thereby provide an unobstructed opening at the proximal end of the basket. A terminal (i.e., distal) end of the basket device can be closed or constricted so as to form a pocket for receiving emboli or thrombotic debris.

The basket device can assume a number of forms. In one presently contemplated aspect, the basket device of the present invention embodies first and second end portions, and a mid-section having a plurality of consecutive rings, each ring having a plurality of generally straight members configured in an alternating V-pattern providing a plurality of proximal and distal apices. In another aspect, the intravascular basket device has a mid-section defined by a single ring also having generally straight members configured in an alternating V-pattern providing four apices on each of the mid-section proximal and distal ends. In yet another embodiment, the mid-section may embody a double ring design configured in a four apex pattern. In other aspects, the basket device mid-section may include rings having different lengths or, in the alternative, include a proximal section having different lengths. In the embodiments, the plurality of members can be curved, S-shaped, angled, tapered etc. rather than straight or can be a combination of straight and curved, angled, tapered or other combinations etc.

Moreover, the present invention embodies a tip for an endovascular device including an atraumatic soft coil for preventing damage to tissue and facilitates advanceability. The tip further includes multiple layers of coiled material to enhance these objectives as well as to provide stiffness variations.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a side view, partially in cross-section, of a vessel occluded by debris and a distal portion of a delivery catheter and intravascular snare assembly of the present invention positioned proximate the debris;

FIG. 2 is a side view, partially in cross-section, of the intravascular basket as deployed within the vessel of FIG. 1;

FIG. 14 is a perspective side view, depicting the device pattern projected onto the tubing which it will be cut from to produce the basket device of FIG. 3; and FIG. 15 is a perspective bottom view, depicting the device pattern projected onto the tubing which it will be cut from to produce the basket device of FIG. 3.

DETAILED DESCRIPTION OF THE PREFERRED EMBODIMENTS

Figure 3:
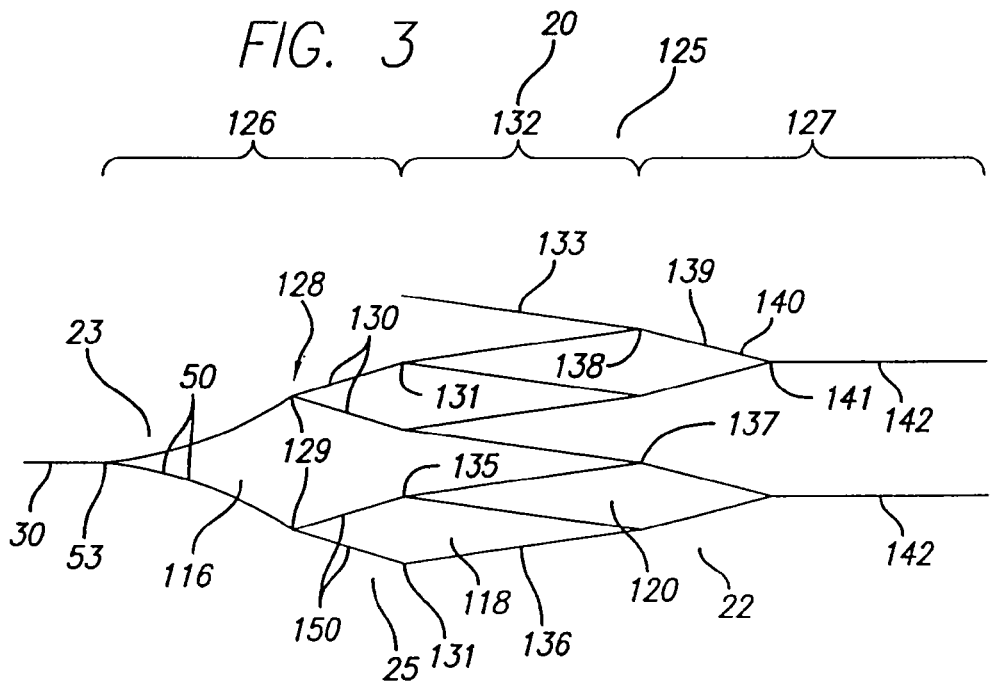
FIG. 3 is a plan view, depicting a pattern of a preferred embodiment of an intravascular basket of the present invention as if the basket was cut longitudinally and unrolled to show its pattern in a flat configuration.

Referring now to the drawings, and in particular FIGS. 1 and 2, there is shown a basket device of the present invention. The basket device 20 is adapted to provide more consistent and improved radial opening as well as enhanced angular resistance to collapse. Moreover, the basket device 20 of the present invention is configured to facilitate the maintenance of clearance in its interior space along its length allowing the material or objects to enter and be captured. Furthermore, since it is contemplated that the basket device 20 be manufactured from a tubular member to form elements with very small widths and thicknesses, the device is thus more easily packed to a relatively smaller diameter and inherently embodies high longitudinal flexibility.

The basket device 20 (FIG. 2) of the present invention includes a body 22 having a proximal end portion 24 and a distal end portion 26. The proximal end portion 24 is intended to be affixed to a terminal end portion of an elongate member 30 (i.e., wire; described in more detail below). In a presently preferred embodiment, the body 22 of the basket device 20 is generally tubular with a proximally directed opening 32 and a generally closed terminal end 34 to thereby form a basket for receiving embolus, stones, thrombus and foreign bodies found in vasculature or other body cavities.

The basket device 20 for intravascular uses is contemplated to be used in conjunction with a generally tubular delivery catheter 40, such as a microcatheter. Additionally, it is contemplated that a conventional guide catheter (not shown) be used in combination with the delivery catheter 40 loaded with a basket device 20. A guide catheter (not shown) is employed to provide a guide within a patient's vasculature through which the delivery catheter 40 is inserted. A proximal end of the guide may include a rotating hemostatic valve or "Y" adapter fitted with sealing hemostatic valves. The basket device 20 is intended to be self-expandable, however, it is possible to employ an expandable member such as a balloon catheter (not shown) to radially expand the basket device that is not self-expandable, but rather must be deformed to assume an expanded configuration.

In use, the body 22 of the basket device 20 is placed proximally in a compressed configuration coaxially within an internal bore of the generally tubular delivery catheter 40. The longitudinally extending elongate member 30 which is attached to the proximal end 24 of the body 22, is likewise coaxially received within the delivery catheter 40. Both the body 22 and elongate member 30 are slidable within the delivery catheter 40 and accordingly, the delivery catheter 40 and the basket device 20 can be displaced longitudinally with respect to each other.

A typical procedure will now be described. In order to restore patency in a vessel, the basket device/delivery catheter assembly 42 is introduced into a patient's vasculature using conventional means such as the Seldinger technique. Sometimes, a cutdown is made to gain access to the patient's vasculature. Using standard endovascular techniques, the emboli in the vasculature is located. The emboli is crossed with an appropriate guidewire (not shown) then the delivery catheter 40. If the vessel is occluded, contrast is injected distal to the occlusion to map the distal vessels. The tip 48 of the delivery catheter 40 is positioned one basket length or slightly more beyond the emboli. The guidewire is removed and the basket device 20 is loaded through a rear hub (not shown) of the delivery catheter 20 with the assistance of an introducer sheath (not shown). The basket device 20 is advanced 30-40 cm and the introducer sheath is then removed.

Next, the basket device 20 is advanced until the tip 26 of the basket is positioned at the distal end of the delivery catheter 40. Radioopaque markers are located on either side of the basket so that the operator can see when the basket is located just inside of the end of the delivery catheter 40. The basket device 20 is held in place by the operator holding the elongate member 30 still while the catheter 40 is retracted to allow the basket device to expand. Holding the basket device 20 in place, the catheter 40 is pulled back until it is proximal to the emboli 46. Then, the basket device is drawn back allowing the emboli 46 to enter the basket device 20. Alternatively, the entire system can be drawn back holding relative positions between the basket device 20 and the catheter 40. This step can be assisted with a "stuttering" technique where the basket device 20 is drawn out a small amount, perhaps 2 mm, then the elongate member 30 is advanced back perhaps 1 mm to allow the mouth of the basket device 20 to re-open fully, thereby assisting clot or emboli entry into the basket. Then the system is drawn out another 1 mm. This is repeated until the basket device 20 has traversed a distance about its own length. To reduce the risk of losing the material contained in the basket or device, blood flow control may be used during extraction. For example, a guiding catheter with a flow control device such as an elastomeric balloon at the distal tip may be employed to slow or stop blood flow past the device during retrieval.

If the emboli 46 is foreign in origin, such as a coil, the basket device 20 can be moved back and forth past the coil in an iterative attempt to engage the coil in the struts of the basket. When this has occurred, the catheter 40 can be advanced causing the basket to collapse and pinch the coil, locking it into one of the openings of the basket device 20. If the emboli is not radiopaque, its position may be checked by a contrast injection and noting a "filling defect." Also, the radiopaque tip 26 of basket device 20 can be observed under fluoroscopy during this process. A pulsing motion can indicate restored flow.

The system 42 is then drawn back until the distal end of a proximal device marker coil (described below) is at the tip of the guide. At this point, a large syringe, perhaps 60 cc, is attached to the guide catheter at the "Y" adapter on the hub. The guide catheter is aspirated as the basket device 20 and emboli 46 are drawn into the guide. Aspiration is maintained until the basket device 20 is fully into the "Y" adapter of the guide catheter, but the basket device 20 is not yet drawn through the hemostatic valve. The "Y" adapter is detached and removed with the basket device in it, allowing a moment of bleed back through the guide to flush any loose emboli. Optionally, then a second "Y" arm is attached to prevent excessive bleed back. The guide is then flushed with saline and the entire procedure repeated as required to remove further emboli.

The manner in which the body portion 22 of the basket device 20 self-expands within the vasculature and the resultant expansion profile provides a number of advantages. In particular, the body 22 expands to conform to the repair site 44. That is, the generally tubular profile of the body portion 22 substantially conforms to the walls defining the blood vessel 49. Alternatively, the basket device 20 can be sized such that upon full expansion it has a diameter smaller than the diameter of the blood vessel 49 if desired. Moreover, the expansion of the body 22 facilitates the maintenance of clearance in its interior space along its length allowing the material or objects 46 to enter and be captured and specifically provides a substantially unobstructed access to the proximally directed opening 32 to the body 22. Significantly, as the body 22 self-expands, members 50 and 51 leading to the opening 32 to the body 22 are angled or oriented so as to be adjacent to the walls defining the blood vessel 49 and are therefore substantially removed from the flow path to thereby provide an unobstructed opening 32.

In its expanded state, the basket device 20 is particularly well-suited to remove embolic or thrombotic debris 46 from the blood vessel 49. As stated, the basket device 20 can be withdrawn proximally so that the debris 46 can be captured by the body 22 of the basket device 20. Alternatively, a separate pusher mechanism (not shown) can be employed to push the debris 46 within the basket defined by the body portion 22. Once the debris has been captured, the system 42 can be removed from the patient's vasculature or the basket device 20 containing the debris 46 can first be pulled within the guide catheter (not shown) and then the assembly 42 removed from the target repair site 44. Also, just the proximal end portion 24 of the basket device 20 can be cinched down to lock the debris without being fully pulled into the delivery catheter 40.

It is to be understood, however, that thrombus or other blood-based material captured within the basket may be eliminated in a variety of ways. For example, the material may be drawn into the guide catheter with the aide of suction applied to the guide catheter, and removed from the body. Also, these materials may be removed from the occluded vessel and allowed to dissolve under natural or induced lytic processes. Alternately, the blood-based material may be inserted into other vasculature more tolerant of occlusion and released.

Figure 3A:
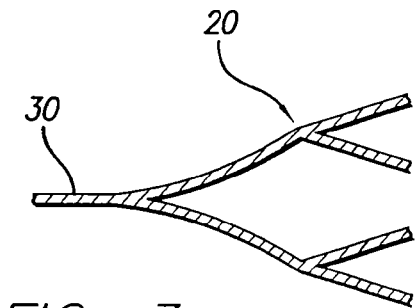
FIG. 3*a* is an enlarged view of a portion of an intravascular basket of the present invention, depicting curvilinear members defining the basket.
Figure 3B:
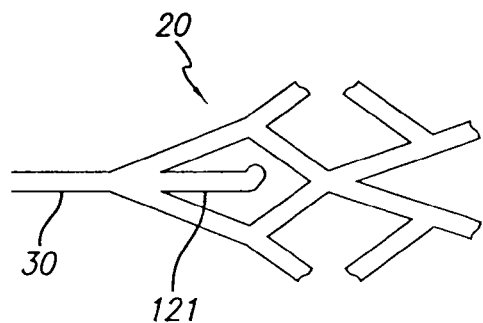
FIG. 3*b* is an enlarged view of a portion of an intravascular basket of the present invention, depicting a filler member positioned between other members defining the basket.

Referring to FIG. 3, in a preferred embodiment of a basket pattern 125 shown as if it was cut longitudinally and unrolled to depict its pattern in a flat configuration, a basket 20 includes a proximal section 126, mid-section 132, and a distal section 127. The sections 126, 132 and 127 together form a substantially tubular basket body 22 with a tapered distal end as will be developed further below. It is contemplated that the body 22 embodying such a pattern 125 be cut from a tubular member using a laser. Alternatively, the body can be made from a flat sheet of nitinol and rolled into a tubular basket body. As best seen in its flattened or unrolled state, the basket pattern 125 further includes an elongate member 30 extending proximally from a proximal end portion 53 of the basket body 22. It is also to be recognized that each of the members defining the basket body 22 in this or other embodiments may have curved, arced, S-shaped, partially straight sections or other configurations (See FIG. 3a, for eg.). Additionally, it is contemplated that the body can further include branches 121 with an enlarged or angled terminal end (FIG. 3b) which act as fillers between other members defining the body 20. Such fillers 121 aid in providing a basket highly equipped to contain material.

The proximal section 126 of the basket 20 includes a proximal end 23, a distal end 25 and a straight member section 128. The straight member section 128 includes a plurality of members 130 generally configured in a V-shape in that the members "fan out" or diverge in a distal direction. In this configuration, the straight members 130 lead to and aid in defining an opening 32 (see FIGS. 2 and 14) to the body 22, when in its as-cut tubular configuration. Therefore, the members 130 of the straight member section 128 are pair-wise configured in a V-shape such that two proximal vertices 129 are formed where the members 130 proximally merge and four open-ended distal end points 131 are provided to define the distal end 25 of the member section 128. It is noted that in the current configuration, the straight member section 128 defines the entirety of the basket proximal section 126, however, as will be subsequently discussed, in alternative embodiments, the proximal section 126 may include a plurality of straight member sections. Finally, the two proximal vertices 129 of the member section 128 merge into two curved members 50. The curved members 50 converge proximally to form a tab 53 that may be connected to an elongate member 30.

The mid-section 132 of the basket pattern 125 may be of a four apex design including a single ring 133 that defines the generally tubular mid-section 132. The ring 133 includes a plurality of straight members 136 configured in an alternating V-pattern forming a plurality of proximal apices 135 and distal apices 137. In order to achieve the four apex design of basket pattern 125, the ring 133 of the basket mid-section 132 may include eight straight members 136 converging end to end in an alternating V-pattern to form four proximal apices 135 and four distal apices 137. Each of the four proximal apices 135 merge into the open-ended distal end points 131 of the straight members 130 of the basket proximal section 126.

The intersection of the four straight members 130 of the basket proximal section 126 and the straight members 133 of the basket mid-section 132 at the proximal apices 135 define a plurality of diamond-shaped apertures 118. Additionally, a single enlarged diamond-like aperture 116, located substantially within the basket proximal section 126, is defined by the intersections at the proximal end of the basket proximal section 126 between the two curved members 50 and the proximal vertices 129 of the basket proximal section 126 and the intersections at distal end of the basket proximal section between the distal end points 131 of the proximal section 126 to the proximal apices 135 of the basket mid-section 132.

Referring still to FIG. 3, the distal section 127 of the basket 20 includes a single straight member section 139 having straight members 140 in a V-shape configuration that "fans-in" (i.e., converge) distally. At the proximal end, the straight members 140 include four open-ended proximal ends 138 (the branches of the V-shape) at the distal apices 137 of the basket 20 mid-section 132. At the distal end, straight members converge to form two vertices 141 at the distally directed members 142. The junction between the two straight members 140 of the basket distal section 127 and the straight members 133 of the basket mid-section 132 at the distal apices 137 define a plurality of diamond-shaped apertures 120.

The distally directed straight members 142 of the basket distal portion 127 may be joined together to form a substantially closed basket. This structure can be joined using soldering or by employing a coil (described herein below) that is wrapped about adjacent structures to form a soft tip. The distally directed extensions 142 may also be trimmed to a desired length.

Another way to describe the basket device is that it begins with a proximal elongate member linked to a series of divergent branches of increasing density covering successively smaller fractions of the tubular circumference. The increasing density of the divergent branches wrap around the circumference from the side where the elongate member ends to form the tube. Linked from the divergent branches is one or more ring segments in which an equal number of struts enter and exit at the joints. Branching from the ring segment is a series of convergent branches of decreasing density covering successively larger fractions of the tubular circumference. This section is tapered down to the distal tip to reduce the required coverage area thus maintaining adequately small openings for encapsulation.

It is noted that the dimensions of a basket pattern may be varied in a number of ways to produce a number of alternative embodiments of the current invention. From these alternative embodiments it will be understood that the lengths of the straight members of the mid-section rings may be varied accordingly to address any specific application requirement. Similarly, the lengths of the generally straight members of the member section of the proximal section may also be varied in length according to the desired design requirement. In order to have the device collapse evenly, all continuous (not recursive) paths from the first bifurcation to the last convergence of members must be of approximately the same length. Otherwise, during collapse the longer members are forced to buckle or the shorter members are forced to stretch to achieve a substantially linear constrained configuration.

Referring to FIGS. 4-7, alternative embodiments of the current invention are depicted. Generally, the basket patterns 145 include a mid-section 148 having two rings 152 and 153 configured in a "four apex" design. Each ring 152, 153 is defined by a plurality of connected vees to thereby define a ring having a generally serpentine pattern. A two ring design having a distal taper may provide enhanced clot capturing capabilities because of the smaller sized apertures located at the distal portions of the basket body 22. In the second and fourth embodiments (FIGS. 4 and 6), the rings 152 and 153 include straight members 155 and 159 having a first length. In the third and fifth embodiments (FIGS. 5 and 7), the rings 152 and 153 include straight members 170 and 174 having a second length that is longer than the first length of straight members 155 and 159. Therefore, the rings 152 and 153 of the second and fourth embodiments are shorter in length than the rings 152 and 153 of the third and fifth embodiments. It is envisioned that the length of the rings of the third and fifth embodiments may be two or more times longer than the rings of the second and fourth embodiments and that there can be any number of rings.

As with the previous embodiment described above, in all four alternative embodiments of basket pattern 145 (FIGS. 4-7), the straight members of each ring are configured in an alternating V-pattern layout to produce four apices on both the proximal and distal ends of each ring. Each ring 152 includes proximal apices 154 and distal apices 156 and each ring 153 includes proximal apices 158 and distal apices 160. The ring 152 is connected to ring 153 at the connection 157 between apices 156 and 158. Together rings 152 and 153 form the generally tubular mid-section 148.

Similar to the first embodiment (as shown in FIG. 3), the basket patterns 145 of the second through fifth embodiments (FIGS. 4-7) includes a proximal section 146 and a distal section 147 configured and connected to the mid-section 148 in a like manner as the first embodiment. As mentioned above, the two ring design of the basket patterns 145 allow for a distally tapering body 22 that provides for the capture of smaller emboli because the additional ring results in a body 22 having an increased number of apertures which are each smaller in size than those of the single ring design.

Figure 4:
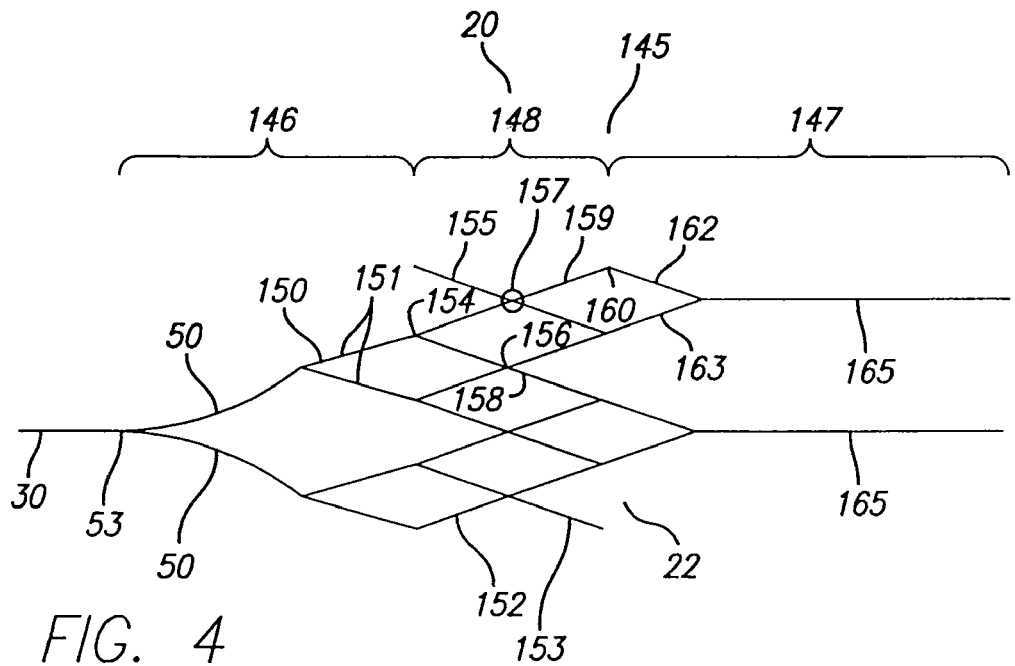
FIG. 4 is a plan view, depicting an unrolled pattern of a second alternative embodiment of an intravascular basket of the present invention.
Figure 5:
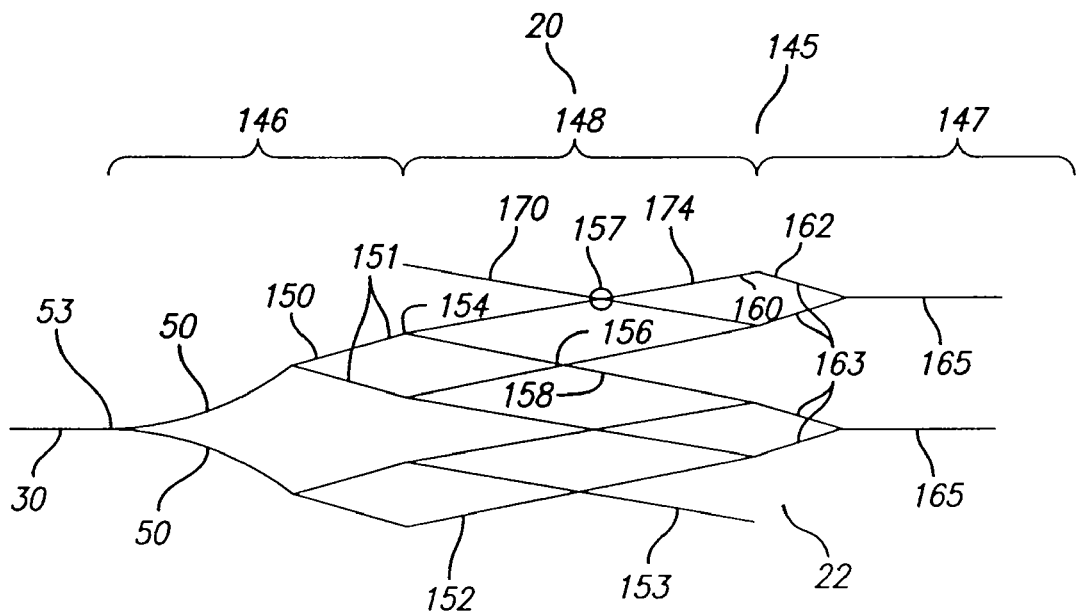
FIG. 5 is a plan view, depicting an unrolled pattern of a third alternative embodiment of an intravascular basket of the present invention.
Figure 6:
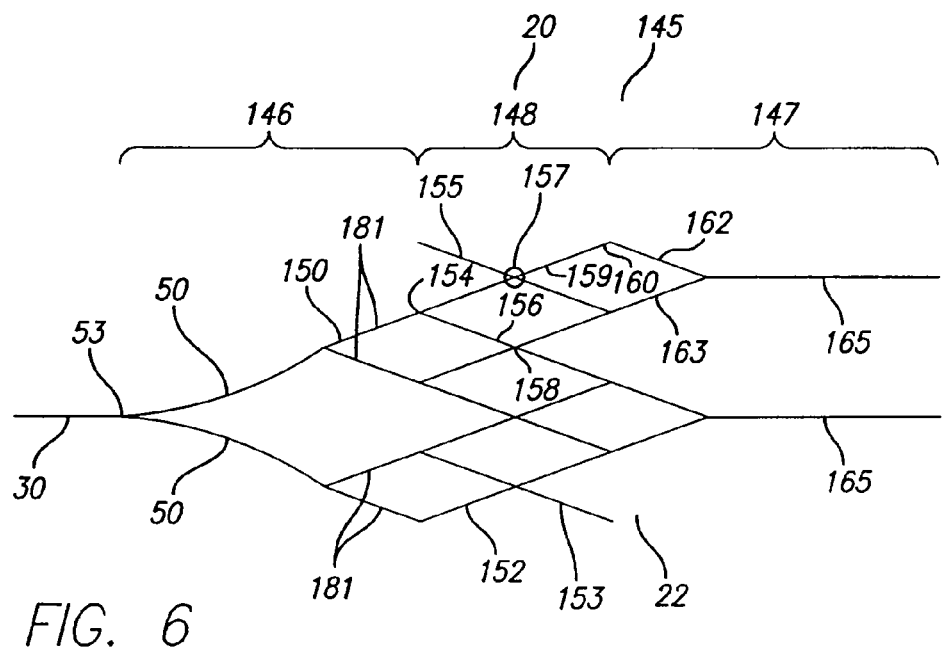
FIG. 6 is a plan view, depicting an unrolled pattern of a fourth alternative embodiment of an intravascular basket of the present invention.
Figure 7:
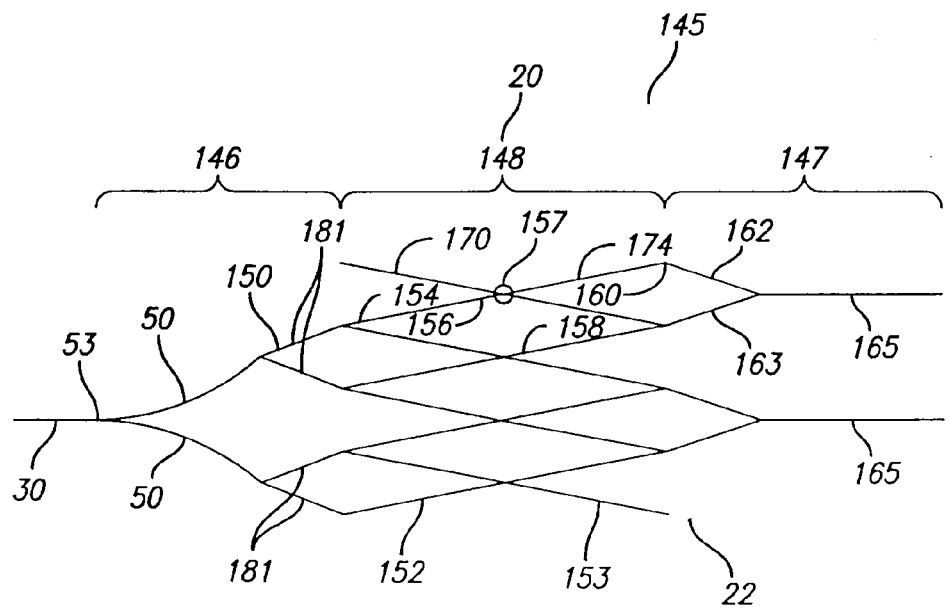
FIG. 7 is a plan view, depicting an unrolled pattern of a fifth alternative embodiment of an intravascular basket of the present invention.

Referring to FIGS. 6 and 7, further variations on the embodiments of FIGS. 4 and 5 respectively are provided. The variations include changes to the proximal transition defining proximal opening 32 of the basket 20. Therefore, in the second and third embodiments (FIGS. 4 and 5), a first member section 150 includes straight members 151 having a first length, while in the fourth and fifth embodiments (FIGS. 6 and 7) the first member section 150 includes straight members 181 having a second length that is shorter than the length of straight members 151. The change in the length of the members of the first member section 150 is intended to increase the radial strength of the device proximally. Therefore, the radial strength of the proximal transition of the device body 22 is increased which improves emboli capture by holding the device open and a shorter tab improves push by providing greater resistance to column buckling.

As can be seen from the various embodiments presented herein, the basket device 20 may be configured having different mid-section 148 or proximal section 146 lengths or may be designed to include different numbers of apices within the mid-section. These changes are only dependent on the design requirements of the physician, and any such modification will not depart from the scope of the present invention.

Figure 8:
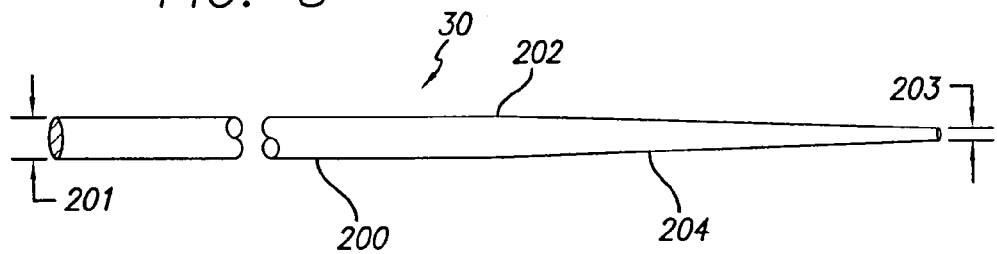
FIG. 8 is a plan view, depicting an elongate member of the present invention.

Referring now to FIG. 8, there is shown one preferred embodiment of the elongated member 30 of the present invention. The member 30 embodies a gradual or step-tapered core comprising a proximal section of 304V stainless steel and a distal section of nitinol or an equivalent material for the intended purpose. A proximal portion 200 of the member 30 has a generally constant cross-sectional profile and a first diameter 201. At a transition point 202, the member 30 begins to taper in a gradual and consistent, alternatively in a step-tapered or in parabolic or other non-linear manner, from the first diameter 201 to a second diameter 203 along a distal end portion 204.

Figure 9:
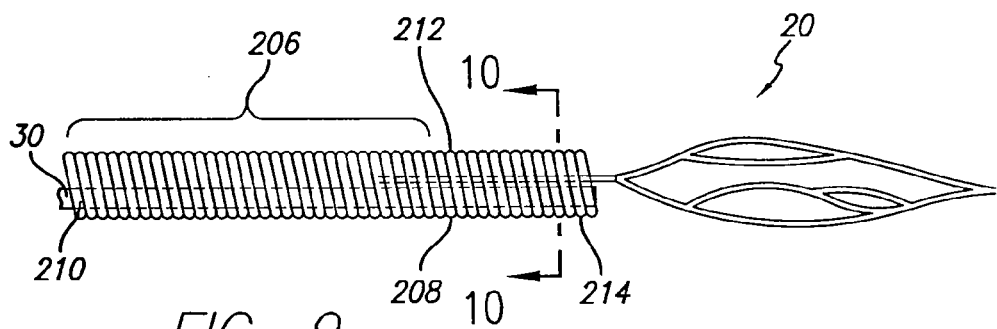
FIG. 9 is a side view, partially in cross-section, depicting a plurality of coils configured about a distal end portion of the elongate members in combination with a basket device of the present invention.
Figure 10:
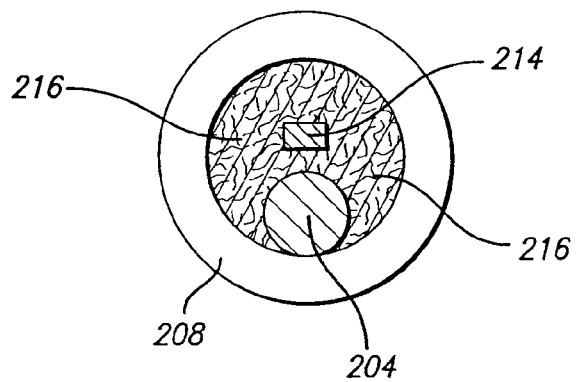
FIG. 10 is a cross-sectional view, depicting the assembly of FIG. 9 taken along lines 10-10.

As shown in FIGS. 9 and 10, a pair of longitudinally adjacent arranged coils 206, 208 are employed to attach a proximal tab 214 of a basket device 20 to the distal end portion 204 of the elongate member 30. The first, proximal coil 206 is contemplated to be composed of 304V stainless steel, the first coil being soldered to the elongate wire 30 near its tapered portion 210. The second coil 208 is contemplated to embody a medical grade radiopaque wire, typically a platinum alloy such as about 90% platinum and 10% iridium alloy. This second coil 208, which serves as a radiopaque marker, is soldered to the elongate member 30 near a distal end portion 212 of the first coil 206. Alternatively, the second coil 208 is soldered to the first coil 206. A proximal tab 214 of the basket device 20 is contained within the second coil 208 and is soldered 216 to the elongate member 30.

Figure 11:
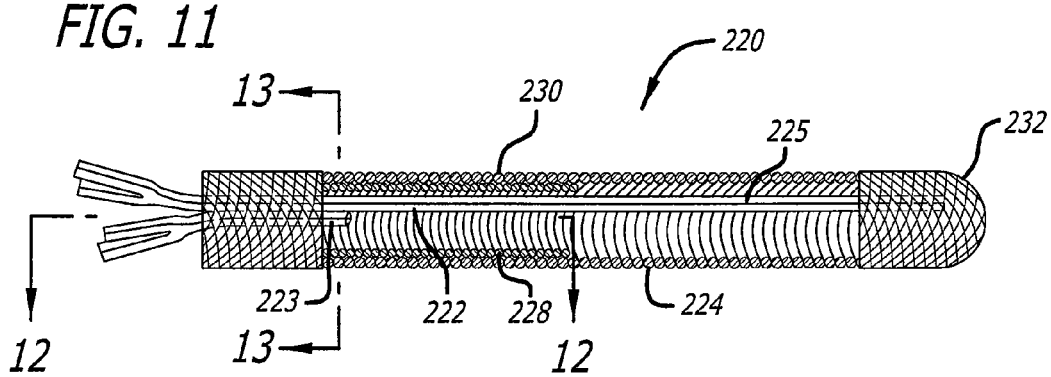
FIG. 11 is a side view, partially in cross-section, depicting a distal end portion of a tip of the basket device of the present invention.
Figure 12:
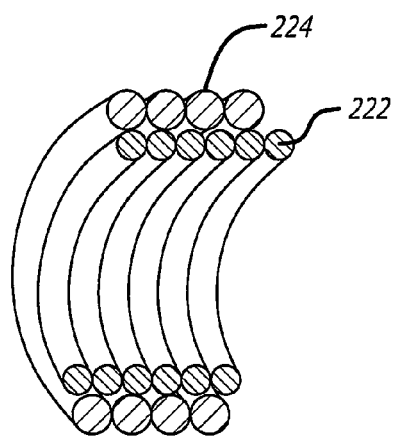
FIG. 12 is a cross-sectional view, depicting a portion of the assembly of FIG. 11 taken along lines 12-12.
Figure 13:
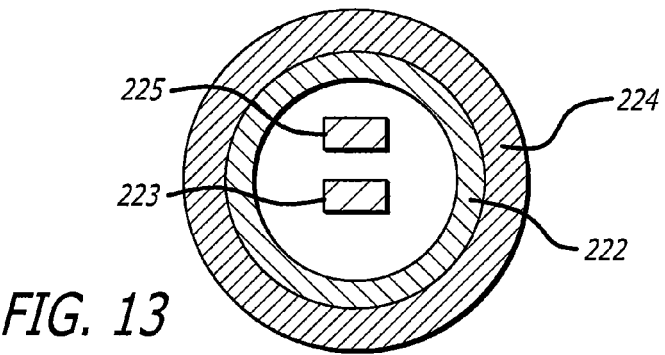
FIG. 13 is a cross-sectional view, depicting the assembly of FIG. 11 taken along lines 13-13.

Turning now to FIGS. 11-13, one presently preferred embodiment of a distal tip portion 220 of the basket device 20 of the present invention is described. The distal tip portion 220 embodies two partially coaxial coils 222, 224, the combination of which retains the distally directed extensions 223, 225 projecting from the body 22 of the basket device 20. The combination also provides a soft atraumatic tip with variable stiffness from softest distally to stiffer proximally. Varying the relative lengths of the tip and coils 222, 224 results in creating changes in stiffness and thus, can be selected to provide the device with desired flexibility.

The inner coil 222 is comprised of nitinol or equivalent material, and begins at a proximal location 226 and extends to a distal location 228. The nitinol inner coil 222 provides kink resistance as well as creates a smooth stiffness transition from the tip of the basket portion of the basket device 20. The outer coil 224 is coaxially configured about a distal portion 230 of the inner coil 222 and is preferably comprised of 90% platinum and 10% iridium alloy or an equivalent combination of materials. As such, the outer coil 224 can operate as a radiopaque marker.

The distal tip portion 220 further includes a rounded terminal end 232 that provides a blunt atraumatic surface. The terminal end 232 embodies a soldered joint which acts in retaining the helical configuration of the outer coil 224.

With reference to FIGS. 14 and 15, a brief summary of the process used to manufacture the basket devices 20 of the present invention is provided, with a specific focus on a second embodiment of the present invention. As shown in FIG. 3, the preferred embodiment of the present invention is relatively similar to the other embodiments disclosed and includes a four apex single ring pattern 125. It is contemplated that the basket devices 20 of the present invention be cut from a tube 240 using a laser. In particular, a specific pattern is programmed into the laser device and the laser is activated to cut the desired pattern into the tubular element 240. The excess tubular components are removed, thereby leaving a manufactured structure such as the basket pattern 125 shown in FIG. 3, corresponding to the desired pattern. In a presently preferred embodiment, a superelastic material such as nitinol is a material of choice for the basket device 20. Thereafter, post-processing such as surface treatment, burr removal, oxide removal and/or shape setting of the manufactured structure is performed. Heat treating is also performed for stress-relief of the device.

In particular, post-processing steps include taking an as-cut device and bead blasting the device with aluminum oxide blasting media. The device is then inspected under a microscope for residual slag. If slag remains, the device is bead blasted again. Thereafter, the device is stress relieved in a molten salt bath without expanding. The device is subsequently heat-expanded in a molten salt bath mounted on a suitable size mandrel. After heat expansion, surface oxidation is removed in an aqua regia bath. When nitinol is the material of choice, the nitinol is etched with HF solution to desired strut size resulting in desired softness. The device is then mounted on a guidewire using coils and solder.

In the case of the pattern 125, the post-processing may include deforming the pattern 125 and then joining together the distal end members 142 for the purpose of achieving a closed basket for receiving debris found in vasculature. Being so configured, the pair of diverging members 50 define an opening 32 to the resultant basket and the elongate member 30 extends from a sidewall defined by the opening.

The basket devices of the present invention each provide improved radial opening compared to prior art loop snares since in an expanded state, the elongate member 30 is positioned substantially out of the flow path. Additionally, the device embodies improved resistance to radial and axial loads compared to prior art loop snares. Moreover, since less deformation is required to produce a desired basket pattern, in that, angles between members are provided by laser cutting rather than from local deformations, for example, there is potentially improved stress distribution along the basket devices of the present invention compared to prior art loop snares. Additionally, a greater reduction in radial profile can be achieved without sacrificing performance and in particular, the device can be used in conjunction with microcatheters. As such, the basket devices 20 of the present invention can be passed through narrow and tortuous vasculature. The applications of the present invention are more widespread than that of conventional snare devices because of greater retrieval characteristics while retaining the deliverability characteristics.

The above described invention is principally conceived to be operational for use in engaging for the purpose of displacing and/or removing material either foreign or native to the body, including partial or complete obstructions embolic and/or thrombotic in nature, from intraluminal or extraluminal spaces of the body including but not limited to intravascular and/or intra-arterial regions of the cerebral vasculature, as well as tubings, stents, or other objects that may or may not be internal to the body. The purpose of the device is to restore functionality of the luminal space or systems dependent on the particular luminal space or as a method of producing any desired effect associated with the removal or displacement of undesirable material.

The intended delivery of the disclosed invention is by means of a commercially available catheter selected for its ability to access the desired location of engagement. The invention may be optimized for specific locations or uses by means of sizing the individual elements in the design and/or the overall dimensions, as well as selection of materials, mesh configuration, number and relative geometry of component members to meet the requirements of the operational space. Optimizations may include tabs protruding from the sides of members to increase coverage of the open areas between members, offsetting vertices of joints to increase packing efficiency, or providing unconnected distal curved path. There may additionally be variations of the dimensions of length, thickness, and width of distal and proximal tabs for joining basket with delivery wire and distal tip to provide smooth stiffness transitions from tip to basket and basket to delivery wire. Such optimizations are means of adjusting operational attributes including: flexibility, applied circumferential force, engagement effectiveness, deliverability and traversal through tortuous vasculature, and volume of material to be engaged.

Alternate or additional materials for the basket portion of the device may include a shape memory polymer thermoset, elastomer, thermoplastic constituents such as nylon, or other metal either pure or alloyed, as well as composite materials such as a combination of glass, aramid, or carbon in a binding matrix. A secondary mesh of the same or dissimilar material may be added to the basket. The wire portion of the device can alternatively be made from a single metal or combination of metals for kink resistance and high flexibility. Either or both components may be tapered to give a transition in stiffness that is appropriate for the vessel in which the invention is to be delivered. The distal tip of the device may incorporate concentric coils made of nitinol, stainless steel, or other metal or plastic to provide a soft flexible atraumatic end.

An alternate method of manufacture of the basket portion of the device may be photo etching, or metal or polymer injection molding or water jet cutting. Furthermore, the device may employ any combination of coatings, agents, or features including those that result from material addition or subtraction to create grooves, bumps, three dimensional patterns, and textures on inner and/or outer surfaces or any combination thereof to promote desired properties such as adherence of materials to be engaged, radiopacity, and low friction between the device and the vessel wall or microcatheter lumen.

In summary, the invention is deliverable to remote regions of the vasculature by gaining access through the use of a guidewire and microcatheter in the vasculature and subsequent deployment of the invention through the lumen of the microcatheter. In a vessel in which flow is impeded or obstructed by material and/or objects including those formed by the body such as blood clot, the device is deployed by withdrawing the microcatheter relative to the elongate wire and basket. Engagement occurs as the system composed of the invention is pulled proximal, causing the basket to encompass the material. After the material has been engaged, removal of the material is accomplished by withdrawing the system into a guide catheter lumen through which the microcatheter is passed with or without simultaneously pulling fluid through the guide lumen or removing the entire system with the guide catheter.

Thus, it will be apparent from the foregoing that, while particular forms of the invention have been illustrated and described, various modifications can be made without the parting from the spirit and scope of the invention. Accordingly, it is not intended that the invention be limited, except as by the appended claims.

What is claimed is:

1. A medical retrieval device for use in a patient's vasculature, comprising:
   an elongate member having a proximal end and a distal end;
   a body attached to the distal end of the elongate member which is configured to engage or capture material found in the vasculature, the body including a distally directed extension; and
   a distal tip portion including a first coil and a second coil which coaxially extend over the distally directed extension of the body.

2. The device of claim 1, wherein the first coil is made from nitinol.

3. The device of claim 1, wherein the second coil is made from an alloy made from about 90% platinum and about 10% iridium.

4. The device of claim 1, further including a weld which connects the distally directed extension to the first coil.

5. The device of claim 1, further including a second distally directed extension which has the first and second coils coaxially disposed thereover.

6. The device of claim 5, wherein the first distally directed extension has longitudinal length which is longer than the longitudinal length of the second distally directed extension.

7. The device of claim 1, wherein the first coil has a longitudinal length and the second coil has a longitudinal length, the longitudinal length of the first coil being shorter that the longitudinal length of the second coil.

8. The device of claim 7, wherein the second coil is coaxially disposed over at least a portion of the first coil.

9. The device of claim 8, wherein the distal end of the first coil is located proximal to the distal end of the second coil.

10. The device of claim 9, wherein the first coil is made from nitinol.

11. The device of claim 10, wherein the second coil is made from an alloy made from about 90% platinum and about 10% iridium.

12. The device of claim 1, wherein at least a portion of the body extends distally from the distal end of the elongate member.

* * * * *